United States Patent [19]
Harding

[11] Patent Number: 5,835,218
[45] Date of Patent: Nov. 10, 1998

[54] MOIRE INTERFEROMETRY SYSTEM AND METHOD WITH EXTENDED IMAGING DEPTH

[75] Inventor: Kevin G. Harding, Ann Arbor, Mich.

[73] Assignee: Insutrial Technology Institute, Ann Arbor, Mich.

[21] Appl. No.: 898,647

[22] Filed: Jul. 22, 1997

Related U.S. Application Data

[63] Continuation of Ser. No. 503,707, Jul. 18, 1995, abandoned.

[51] Int. Cl.$^6$ ........................................................ G01B 9/02
[52] U.S. Cl. ..................... 356/354; 356/374; 250/237 G
[58] Field of Search .................................. 356/354, 359, 356/360, 374, 376; 250/237 G

[56] References Cited

U.S. PATENT DOCUMENTS

| | | |
|---|---|---|
| 4,794,550 | 12/1988 | Greivenkamp, Jr. . |
| 4,981,360 | 1/1991 | Schwarz . |
| 5,069,548 | 12/1991 | Boehnlein . |
| 5,075,562 | 12/1991 | Greivenkamp, Jr. ..................... 356/374 |
| 5,307,152 | 4/1994 | Boehnlein et al. . |

OTHER PUBLICATIONS

"Analysis of Rotating structures using image derotation with multiple–pulsed lasers and moire techniques", J.C. MacBain, W. Stange, Kevin Harding, Optical Engineering, vol. 21, No. 3, pp. 474–477, (May/Jun. 1982).
"Moire Interferometry for Industrial Inspection", Kevin Harding, Lasers & Applications, pp. 73–78, (Nov., 1983).
"Phase Grating Use in Moire Interferometry", Kevin Harding and Steven Cartwright, Applied Optics, vol. 23, No. 10, pp. 1517–1520 (May 1984).
"Optical Examination of Highly Curved Structures", Kevin Harding, SPIE, vol. 814 Photomechanics and Speckle Metrology, pp. 406–412 (1987).
"Phase Grating Use for Slope Discrimination in Moire Contouring", Kevin Harding, SPIE, vol. 1614, Optics, illumination and Image Sensing for Machine Vision, VI, pp. 265–270 (1991).
"Optical Moire Leveraging Analysis", Kevin Harding, SPIE, vol. 2348, Optics, Illumination and Image Sensing for Machine Vision IX, (Nov., 1994) (8 pages).
Patent Abstracts of Japan, vol. 6, No. 248 (P–160) & JP, A, 147003 (Nippon Demki K.K.), Dec. 7, 1992, Sep. 10, 1982.

*Primary Examiner*—David C. Nelms
*Assistant Examiner*—Robert Kim
*Attorney, Agent, or Firm*—Harness, Dickey & Pierce, PLC

[57] ABSTRACT

A moire interferometry system and method are provided for achieving full field surface contouring with an extended depth of view of image. The moire interferometry system includes a projection system generally made up of a light source, imaging lens and a square wave grating pattern. The imaging lens is configured to filter higher order light rays passing through the square wave grating pattern so as to project a sine wave like pattern onto a desired surface. The moire interferometry system also includes a viewing system generally made up of an imaging lens, a submaster grating and a camera. The submaster grating is preferably a customized grating that may be produced by recording a grating pattern in relation to a reference surface. The camera is able to view an image anywhere within the extended depth of image and analyze the moire fringes. A determination of deviation between a test part and a reference surface provides a part inspection system.

19 Claims, 4 Drawing Sheets

MOIRE INTERFEROMETRY SYSTEM AND METHOD WITH EXTENDED IMAGING DEPTH

This is a continuation of U.S. patent application Ser. No. 08/503,707, filed Jul. 18, 1995 now abandoned.

BACKGROUND OF THE INVENTION

1. Field of the Invention

The present invention generally relates to surface contour detection and, more particularly, to a moire interferometry system and method for detecting surface contour over a large surface and with an extended depth of view of image.

2. Discussion

Surface measurement techniques are particularly useful for inspecting panels of sheet metal or other materials for the presence of defects by attempting to distinguish shape anomalies such as dents, flat spots, creases and waviness. There are a variety of non-contact approaches for measuring the surface contour of an object. Conventional inspection techniques include visual inspection aided by a glossy finish on the surface and use of a colored fluorescent tube. Other approaches include range finding techniques such as line of light profiling, stereo viewing and shape from shading. However, these conventional approaches are generally subjective in nature and susceptible to a number of problems.

Another approach, known as moire interferometry, provides full-field process data with gray scale values which can generally be made insensitive to lighting variations, dirt, and other non-shaped parameters. Moire interferometry is a full-field noncontact method of measuring out-of-plane displacements for in-plane deformations of a structure. A typical moire interference pattern is a series of light and dark fringe lines of equal change in surface position which map out the contour change of an object much the same way a topography map delineates the contour of land. The moire interferometry fringes are formed by overlaying two gratings, one grating on the object, and a reference grating through which the object is viewed. The moire pattern is created by the overlay of maxima and minima of the two gratings. A camera or other viewing means views the grating lines on the surface through the submaster grating lines.

One example of a moire interferometry system is described in detail in U.S. Pat. No. 5,307,152 entitled "Moire Inspection System", which is hereby incorporated by reference. The above-referenced system includes a projection system having a light source, grating and projection lens for projecting grating lines onto a surface. In addition, the moire interferometry system further includes a pair of viewing systems, each including a camera lens, imaging lens and submaster grating for viewing the grating lines on the surface through the submaster grating lines. The camera obtains an image of the viewed grating lines and determines a moire pattern which is then used to compare the contour of the surface to a golden part to determine if defects exist. The sensitivity of a moire pattern to be able to map the shape of a surface is affected by the viewing and projection angles as well as the period of the grating on the test surface.

Unlike known line of sight systems, the depth of resolution of moire is typically not limited by the camera resolution. The sensitivity in moire interferometry can be adjusted to fit application requirements and is generally very tolerant to positioning errors or extraneous motions. However, known moire interferometry techniques can require greater demands on the optical system than other available methods. Furthermore, prior moire interferometry systems generally have not been adapted for large panel inspection with an extended depth of view. Instead, known systems are generally capable of performing range measurements on small areas and within a relatively narrow depth of view.

Generally speaking, a larger angle between projection and viewing systems provides more sensitivity to the moire pattern. Likewise, a finer grating period will enhance the sensitivity. The desire to have high sensitivity, particularly over a large surface area, has generally been limited by the need to work at high angles to the part surface or to image a fine grating over a large surface. In order to maintain a geometrically correct image both on and off the part surface, the optical axis of the projection and viewing lens needs to be near normal to the test surface. This condition would permit a grating of uniform period to be projected onto the surface and then reimaged to a submaster grating of uniform period to create a correct contour map of the part. With a finer period, the depth of field as well as the depth of view of the grating on the part decreases as the usual expression of optical depth of field. If a large and varying shape part is to be viewed, only a shallow region of contour will generally be in focus at one time.

Another limiting factor in obtaining clear moire contour patterns involves the nature of the standard gratings that are generally employed. A number of systems employ grating lines configured in a square wave pattern for producing light and dark square wave lines on the part surface. However, a square wave pattern has a primary frequency associated with the period and also has higher harmonics of frequencies associated with finer patterns which define sharpness of the square edges. When two square periodic patterns are overlaid, the resulting beat pattern generally does not appear as a smooth pattern, but instead has jagged intersections of multiple patterns at different frequencies which can be difficult to separate and analyze. Alternate use of a grating which has a sine wave pattern could be used; however, sine wave grating patterns are generally difficult to manufacture consistently and are not widely available as simple periodic grating patterns.

Thus, it is desirable to provide for a moire interferometry system and method which offers full-field surface detection with an extended depth of view of the image.

More particularly, it is desirable to provide for a moire interferometry panel inspection system and method which efficiently passes a sine wave pattern and extends the depth of view of the image to form a clean moire pattern.

It is also desirable to provide for a moire interferometry system and method which produces a good interference pattern behind a submaster grating and allows for a high angle viewing system.

It is further desirable to provide for such a moire interferometry system and method that allows for the use of a customized submaster grating which produces a good interference pattern.

SUMMARY OF THE INVENTION

In accordance with the teachings of the present invention, a moire interferometry system and method are provided. A projection system is included which has a light source, a master grating and an imaging lens. The master grating has an array of grating lines for projecting lines of the master grating onto the surface. A viewing system is also included for viewing the master grating lines on the surface through a submaster grating. The viewing system includes an imaging lens, an array of periodic grating lines on the submaster grating and a camera for viewing the beat pattern generated at the submaster grating. The intersection of the projected lines on the surface and the lines on the submaster grating produce moire fringes. The viewed moire fringes can be processed and analyzed to determine surface contour information and can be compared to a reference surface to determine if defects, generally corresponding to dimensional deviations, are present in a test surface. According to the present invention, the master grating produces a square wave grating pattern. The higher diffracted orders are filtered out with the imaging lens of the projection system so as to produce an array of sine wave like pattern lines which are projected onto the surface. This filtering removes interference from high diffracted orders and produces an extended depth of view of the image with which the camera may focus to view the grating lines on the surface.

The submaster grating of the present invention is preferably a customized grating that is formed in relation to a reference surface. More particularly, the submaster grating is preferably photographically recorded while viewing a reference surface. This compensates for any distortion which may otherwise be present, such as when the imaging lens of the projection system is tilted. Additionally, the submaster grating produces a good interference pattern, allows for a high angle viewing system and enhances the depth of view for a sine wave pattern to form a clean moire pattern.

BRIEF DESCRIPTION OF THE DRAWINGS

Other objects and advantages of the present invention will become apparent to those skilled in the art upon reading the following detailed description and upon reference to the drawings in which.

DETAILED DESCRIPTION OF THE PREFERRED EMBODIMENTS

Figure 1:
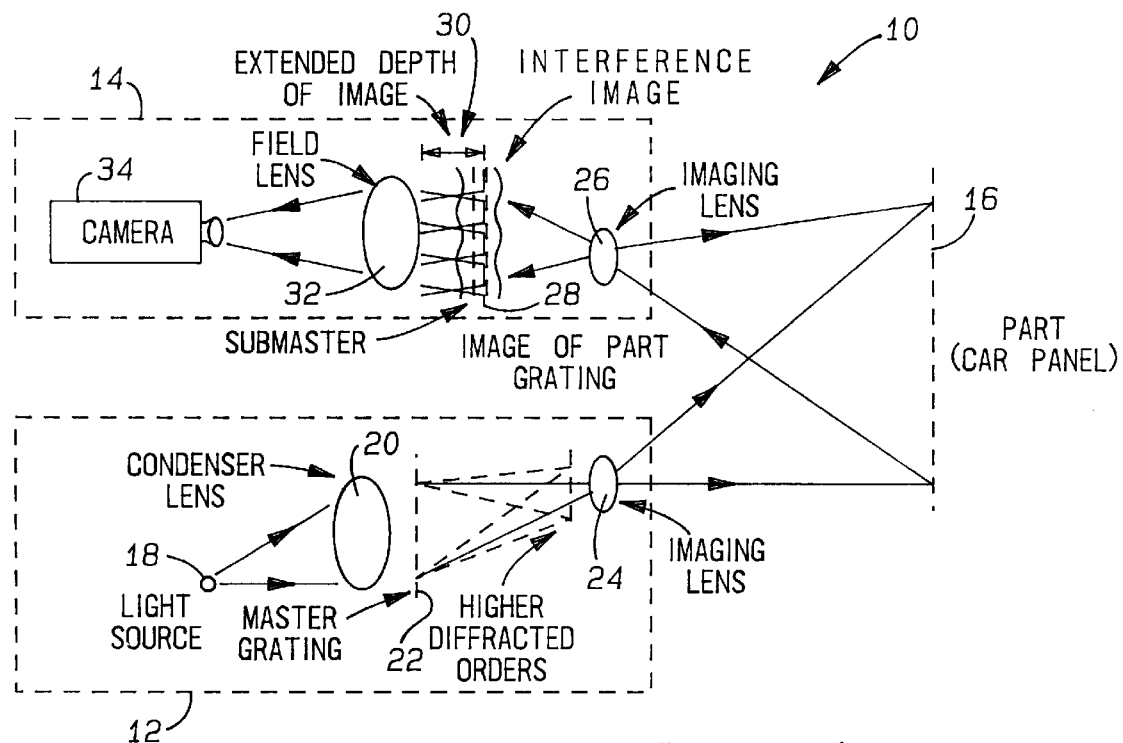
FIG. 1 is a schematic diagram of a moire interferometry system for achieving an extended depth of view of image in accordance with the present invention.

Turning now to FIG. 1, a moire interferometry system 10 is shown in accordance with the present invention. The moire interferometry system 10 generally includes a projection system 12 and a viewing system 14, both focused on the surface of a part 16 to be inspected. The projection system 12 is arranged to project grating lines on the surface of part 16 while the viewing system views the grating lines from a different angle. Since moire interferometry is a full-field detection technique, the contour of an entire area of an object can be mapped out with the moire interferometry system 10 at one time. For example, an automobile panel can be inspected with full-field contouring which is inherently much faster than the known point-by-point or line-by-line contouring techniques and potentially permits on-the-fly surface contour measurements.

The projection system 12 generally includes a light source 18 positioned in front of a condenser lens 20. The light source 18 may include a halogen source or an arc lamp source of the type which produces a white light, for example. The projection system 12 further includes a periodic master grating 22 with periodic square wave grating lines located between the condenser lens 20 and an imaging lens 24. The condenser lens 20 collects and focuses the light through the master grating 22 and imaging lens 24. In turn, imaging lens 24 filters and focuses the light passing through master grating 22 and along a projection angle onto the surface of part 16. Accordingly, an array of light and dark lines are imaged or projected onto the surface of part 16.

Figure 2:
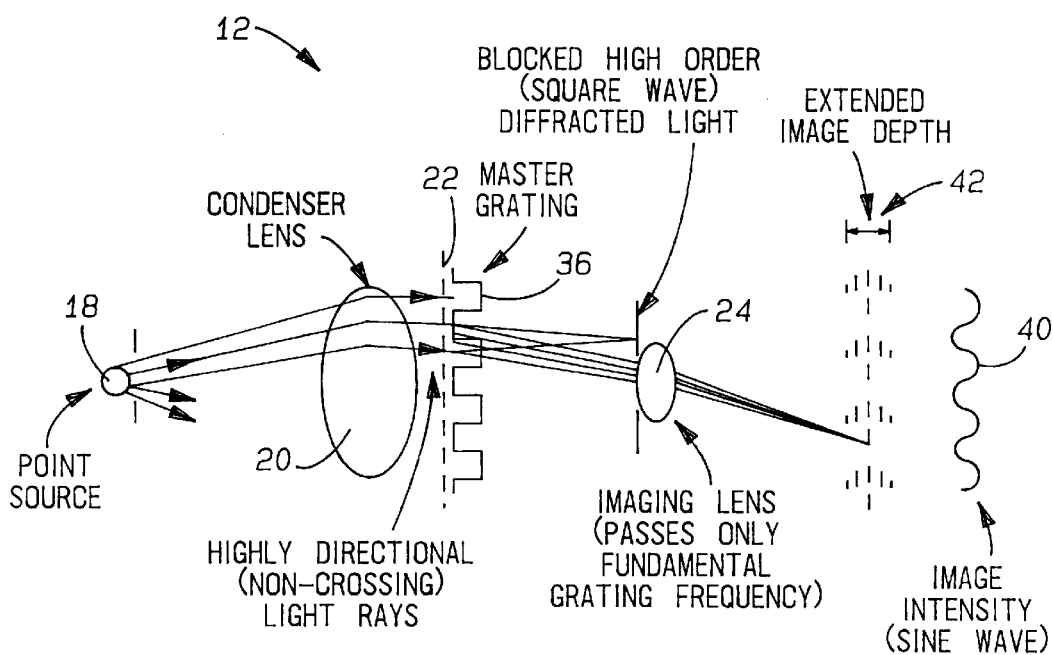
FIG. 2 is a schematic diagram illustrating the projection system of the moire interferometry system shown in FIG. 1.

The projection system 12 according to the present invention is shown in greater detail in FIG. 2. The condenser lens 20 collects the received light rays and focuses highly directional, and preferably substantially non-crossing, light rays through the periodic master grating 22. The master grating 22 has an array of closely spaced periodic square wave grating lines which produces light and dark square wave lines when illuminated. The square wave grating pattern includes an array of closely arranged parallel square wave grating lines which has a preferred period on the order of the near field diffraction range for visible light. Preferably, the period is approximately 50 microns or less for use with white light, but may vary to accommodate light rays of various wavelengths. According to one example, master grating 22 may include a chrome on quartz type grating.

As previously mentioned, a square wave pattern generally has a primary frequency associated with the period. Also, the square wave pattern has higher harmonics of frequency generally associated with finer patterns which define the sharpness of the square edges. Accordingly, the square wave pattern of master grating 22 produces diffracted light rays which include a primary frequency generally associated with a sine wave pattern and higher order diffracted rays generally associated with the square edges of the square wave pattern. The first diffracted order, which is the one closest to the original direction of the light rays, generally contains the information about the fundamental or primary frequency of the master grating 22. According to the present invention, the imaging lens 24 is configured so as to pass the fundamental grating frequency associated with the primary frequency, while removing higher order diffracted light rays.

To achieve filtering of higher order diffracted light rays, the imaging lens 24 preferably has a modulation transfer function which restricts information to a sine wave pattern. This in turn filters out high frequency components. Accordingly, only those light rays associated with the sine wave pattern are able to pass therethrough and be projected or imaged onto the surface of part 16. As a consequence, the higher order diffracted light rays are filtered from the light projection, thereby reducing or eliminating the occurrence of jagged intersections of multiple patterns or different frequencies which may otherwise exist and which would be difficult to separate and analyze.

For purposes of collecting sufficient light, the diffracted orders of the master grating 22 might not be separated enough to pass only the desired sine wave information. The separation of the sine wave pattern can be further enhanced by using an imaging lens 24 which has an impulse response that is preferably just beyond the primary frequency of interest. That is, the performance of the imaging lens is designed so that the lens will create a good image of the primary frequency while dropping off quickly at higher frequencies so as to round off the corners and not reproduce the square wave pattern of the master grating 22. This provides for an improved fundamental sine wave pattern projection onto the surface of part 16. Accordingly, the imaging lens 24 operates as a frequency filter in the image formed. This filtering effect may be achieved either by customizing the performance of the imaging lens 24 or by stopping down the lens 24. However, stopping down the lens 24 may cause less light to pass therethrough.

Figure 3:
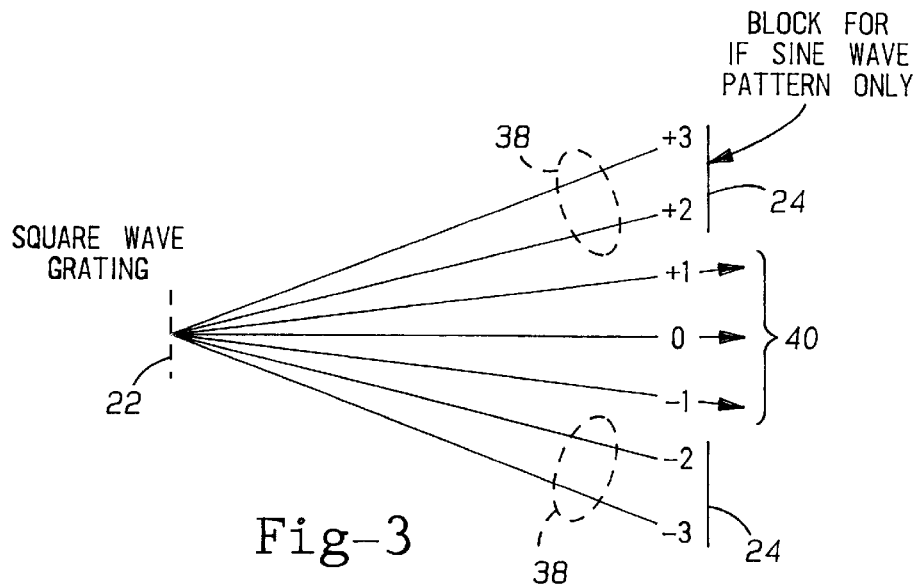
FIG. 3 illustrates filtering of higher diffracted orders which are produced by a square wave grating and filtered with an imaging lens.

With particular reference to FIG. 3, an example of the diffracted light rays including the various diffraction orders and filtering of higher orders are illustrated therein. The primary frequency associated with the sine wave pattern is generally contained within the +1, 0 and −1 diffracted orders as represented by reference numeral 40. Primary frequency light rays 40 are able to pass through the imaging lens 24, while the higher order diffracted light rays such as +2, −2, +3 and −3 orders, as represented by reference numeral 38, are filtered by the imaging lens 24.

The projection of the primary frequency thereby further provides an extended image depth 42 with an image intensity as shown by sine wave 40 in FIG. 2. The sine wave pattern is in fact formed as a white light, common path interference pattern. The depth of the projected interference pattern is affected by the degree of coherence of the source and optical lenses, that is how directional, as well as the distance at which it is formed. This effect creates an image with an extended depth-of-field. The directionality of the light rays also helps this enhanced depth by means of a shadow effect beyond the master grating 22, but the interference effect actually creates a volume image of the initially flat grating pattern.

The viewing system 14 generally includes an imaging lens 26 and a field lens 32 optically coupled to one another for viewing the imaged surface of part 16. A submaster grating 30 is displaced between the imaging lens 26 and field lens 32 for creating an interference image. The viewing system 14 further includes a camera 34 for viewing an image of the grating lines on the surface of part 16 as directed through the field lens 32 submaster grating 28 and imaging lens 26. Camera 34 may include image acquisition, image processing and image display hardware, as well as a display for viewing by a user. The viewing system 14 processes viewed images and determines surface contour measurements and is able to compare surface measurements to a reference surface to determine if defects are present in a given surface.

Figure 4:
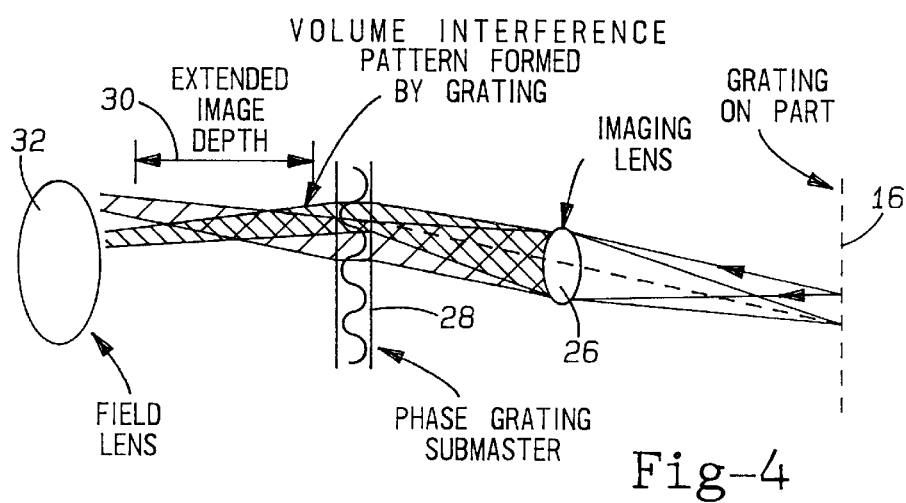
FIG. 4 is a schematic diagram illustrating the viewing system of the moire interferometry system.
Figure 5:
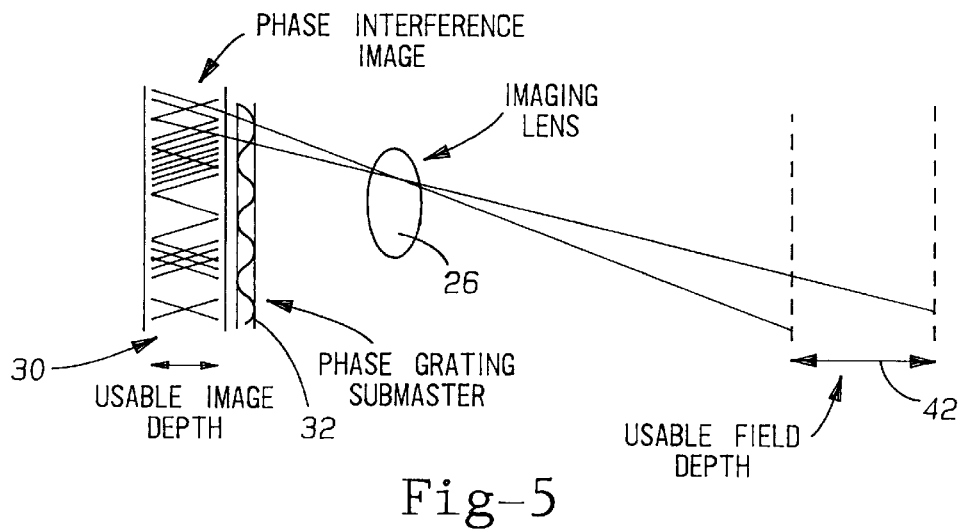
FIG. 5 is a schematic diagram illustrating an enlarged view of a portion of the viewing system.

The viewing system 14 is further illustrated in greater detail in FIGS. 4 and 5. FIG. 4 shows the effect of creating an interference pattern grating on a part which is imaged back, while FIG. 5 is an enlarged view of the phase image which shows there is a large usable field depth 42. Referring to FIG. 5, generation of the volume interference image over the extended image depth 30 by means of the phase grating submaster 28 is illustrated. The effect of this interference image is a submaster grating 28 that exists through a volume in space behind the submaster phase grating 28 which provides the extended usable image depth 30. This volume interference image overlays any image coming from the part field over the extended field depth 42 as shown. With particular reference to FIG. 4, the light coming from the master grating 22 that has been projected onto the part surface 16 interacts with the phase grating submaster 28 to form a moire beat pattern by means of white light interference through the extended range of the image behind the phase grating submaster 28. By this mechanism, the submaster grating 28, as shown in FIG. 5, interacts with the image of the part grating throughout the volume submaster grating depth, so as to modulate the submaster grating pattern into a beat pattern which is the product of both the submaster volume grating and the part grating. The resulting pattern is the moire of the difference between the two patterns and provides the contour information about the part 16.

The submaster grating 32 is a phase grating which is preferably formed with reference to a reference or "golden part". That is, upon viewing a reference or golden part, a phase grating pattern is formed and used as the submaster grating 32. Since the projected image on part 16 is a sine wave pattern, the submaster grating 32 will contain a grating pattern in relation to the sine wave pattern that is projected onto the surface of part 16. The grating pattern of grating 28 may vary from the sine wave pattern depending on the contour of the surface of the reference surface, the angle of projection and viewing angle, as well as the angle of tilt of imaging lens 24.

The optical moire interferometry system 10 of the present invention is used as a filtering and modification system. A part can be viewed at an angle beyond the field angle of a lens by tilting the imaging lens 24 toward the area being viewed. However, this tilting of imaging lens 24 may make the image of a uniform grating become distorted. By recording the submaster grating 28, through this tilted system off a reference surface, the effect of any such distortion can be removed from the resulting contour of a test part. If the reference is a flat plane, then the contour compares the test part to a plane. Alternately, the reference surface might be a golden part, or even a geometric shape such as a cylinder or sphere. To be effective, the submaster grating 28 preferably records by a medium that is designed or processed to provide a highly linear response over a wide range of intensities and frequencies of grating. A photographic process using a 1:16 dilution of a high contrast developer, such as an HRP developing chemical, manufactured and sold by Kodak, can be used to create such an effect. Some forms of photopolymers, photoplastics, and phase recording crystals and other media may also be used to this effect.

The submaster grating 28 as shown in FIG. 4 is a phase grating submaster which creates a volume interference pattern 30 over an extended image of depth. Preferably, the submaster grating 28 has a very fine period of 50 microns or finer so that white light, for example, hitting the flat submaster grating 28 will create a white light diffraction pattern in a volume behind the submaster grating 28. For improved results, a grating pattern of 15 to 20 microns may alternately be used. A black and white amplitude grating, which is often made as a photographic recording, could be employed for the submaster grating 28. However, employment of a phase grating for submaster grating 28 can provide enhanced light and diffraction efficiency over a black and white amplitude grating.

With the use of the viewing camera 34, an image of the grating lines as seen on the part 16 is taken from anywhere within the extended volume of the interference pattern 30 behind the submaster grating 28. The interference pattern 30 allows for realization of an extended depth-of-view of the two dimensional grating on the part 16. The interference effect creates a sine wave like pattern, as higher diffracted orders are actually focused at different distance from the grating. Accordingly, one pattern can be selected so that the rest are essentially out of focus. With the use of viewing camera 34 and associated processing hardware, the moire fringes may be examined and processed. Furthermore, the pattern examined between a reference part and a test part can be compared so as to inspect for defects which may exist on the surface of the test part.

Figure 6:
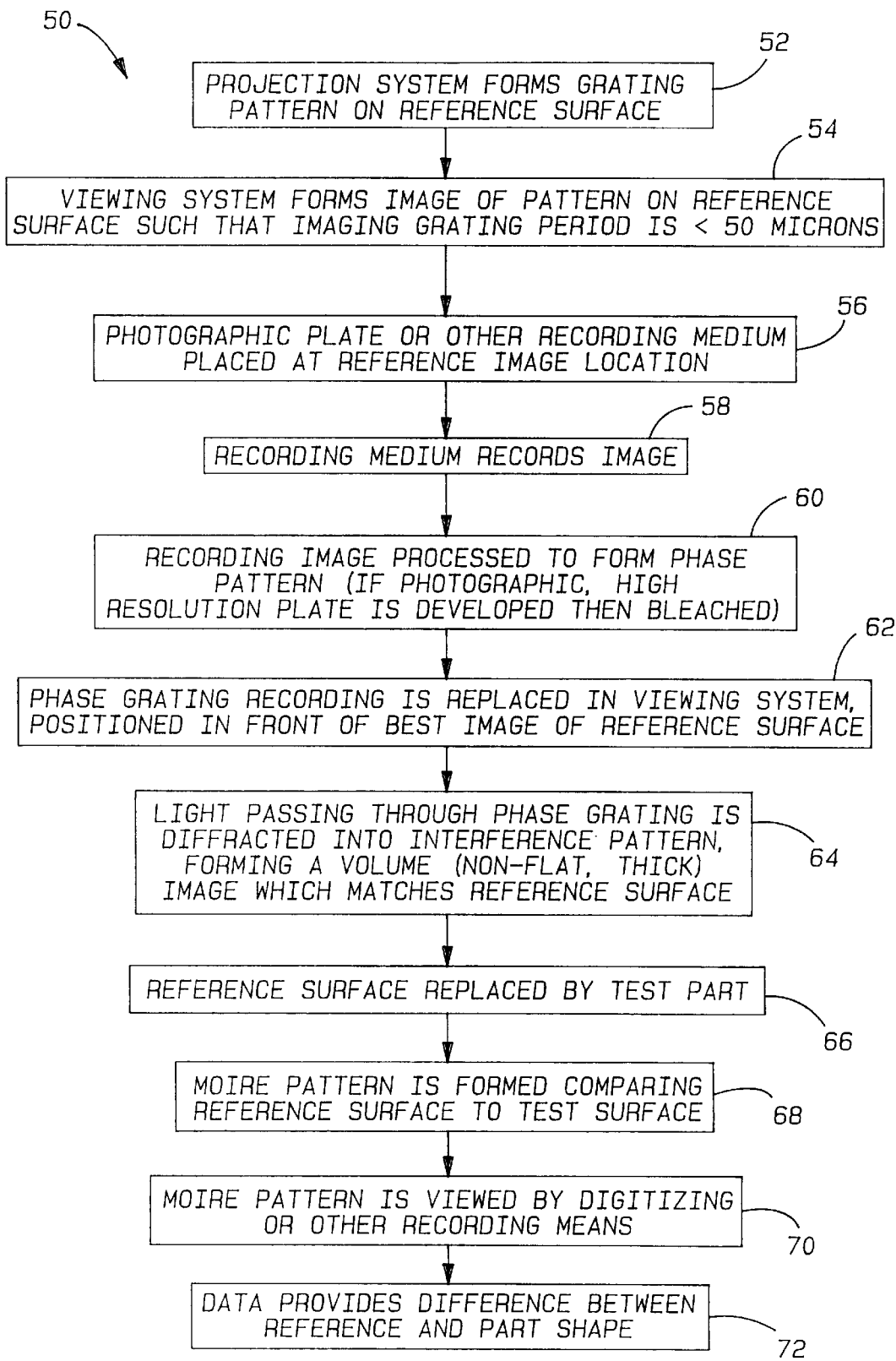
FIG. 6 is a flow diagram illustrating a methodology for creating and using a submaster phase grating in accordance with the present invention.

Referring now to FIG. 6, a methodology 50 of forming the customized submaster grating 28 and inspecting the shape of a part in contrast to a reference surface is illustrated therein. The methodology 50 begins at step 52 whereby the projection system 12 forms a grating pattern on the reference surface. The viewing system 14 simultaneously forms an image of the pattern on the reference surface so that the imaging grating period is preferably less than 50 microns as shown in step 54. Pursuant to step 56, a photographic plate or other recording medium is placed at the reference image location and the recording medium records the image as provided in step 58. According to one embodiment, the recording image is processed to form a phase pattern pursuant to step 60. Alternately, if a black and white amplitude grating is used, a high resolution plate is developed and bleached pursuant to a bleached photographic recording.

Hence, a phase grating or amplitude recording is replaced in the viewing system 14 and positioned in front of the best image of the reference surface according to step 62. In step 64, light passing through the submaster phase grating 28 is diffracted into an interference pattern 30, thereby forming a volume image which matches the reference surface. The interference pattern 30 offers an extended view of depth of image. Accordingly, the submaster grating 28 is formed to match the particular contour of a reference surface prior to testing the surface contour of a test part.

Once the submaster grating 28 has been formed, the reference surface may be replaced by a test part as provided in step 66. The test part may then be inspected in relation to the surface contour of the reference surface. In doing so, a moire pattern is formed which provides a comparison of the reference surface to the test surface as provided in step 68. In step 70, the moire pattern is viewed by digitizing or other recording means. The gathered data then provides information which can be used to identify the surface contour differences between the reference surface and the part shape as shown in step 72.

Figure 7:
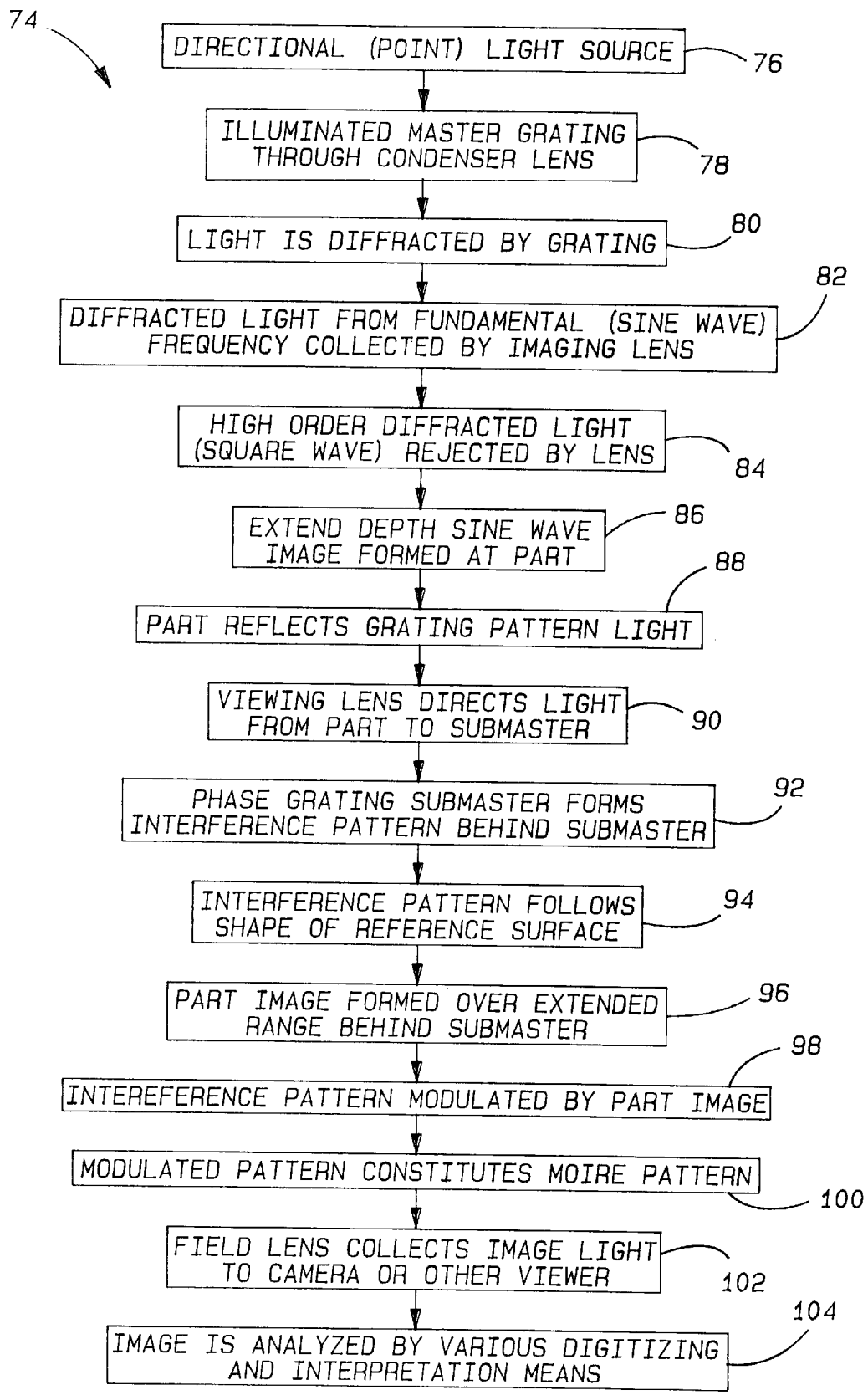
FIG. 7 is a flow diagram illustrating a methodology for detecting surface contours with the extended depth moire interferometry system in accordance with the present invention.

Turning to FIG. 7, a methodology 74 of performing moire interferometry testing with the moire interferometry system 10 of the present invention is provided therein. The methodology 74 begins at step 76 where a directional or point light source 18 illuminates the square wave grating lines of master grating 22 through condenser lens 20 as shown in step 78. Due to the square wave grating lines of master grating 22, light rays are diffracted by the master grating 22 as provided in step 80. In step 82, diffracted light rays from the fundamental sine wave frequency are collected by the imaging lens 24, while higher order diffracted light rays are rejected by imaging lens 24. This provides an extended depth sine wave like image projection at the surface of part 16, while higher diffracted orders generally associated with the edges of the square wave pattern are filtered and thereby prevented from illuminating the imaged surface of part 16.

In response to the projection of the light and dark grating lines on the surface of part 16, part 16 reflects the grating pattern light as provided in step 88. The imaging lens 26 of the viewing system 14 directs the reflected light rays from part 16 to the submaster grating 28 as shown in step 90. The phase grating submaster 28 thereby forms an interference pattern behind the submaster grating 28 as illustrated in step 92. In step 94, the interference pattern follows the shape of the reference surface from which the submaster grating 28 was previously formed. The part image is formed over an extended range behind the submaster grating 28 as provided in step 96. An interference pattern is thereby modulated by the part image according to step 98 and the modulated pattern constitutes a moire pattern as provided in step 100. Field lens 32 collects image light to the camera 34 or other viewing means in step 102. Finally, the image is analyzed by various digitizing and interpretation means pursuant to step 104.

It should be appreciated that the analyzed data may be used to detect defects present in the test part as referenced to the reference surface. This is generally accomplished by analyzing the recorded moire fringes and measuring deviations between the test part and the reference surface to provide a three-dimensional surface comparison. This allows for the system 10 and method to perform part inspections with a full field extended depth of view of image.

While this invention has been disclosed herein in connection with a particular example thereof, no limitation is intended thereby except as defined in the following claims. This is because a skilled practitioner recognizes that other modifications can be made without departing from the spirit of this invention after studying the specification and drawings.

What is claimed is:

1. A moire interferometry system for measuring the shape of a contoured surface, said system comprising:

a projection system including a light source and a first periodic diffraction grating for projecting grating lines onto the contoured surface, said first periodic grating having a first array of square wave grating lines for producing square wave lines, and said projection system further including an imaging lens having a selected modulation transfer function, said imaging lens disposed between the first diffraction grating and the surface for filtering higher diffraction orders of said square wave lines so as to produce an array of sine wave like grating lines on said surface and provide an extended depth of view of image; and a viewing system including a second periodic diffraction grating having a second array of grating lines, said viewing system further having a means for viewing the grating lines projected on said surface through said second array of grating lines within the extended depth of view of image, the intersection of the projected lines on the surface and the lines on the second periodic diffraction grating producing moire fringes.

2. The moire interferometry system as defined in claim 1 wherein said means for viewing comprises a camera focused within the extended depth of view of image.

3. The moire interferometry system as defined in claim 1 wherein said imaging lens is tilted with respect to the contoured surface so as to permit viewing at an angle in excess of a field angle of the imaging lens.

4. The moire interferometry system as defined in claim 1 wherein said second diffraction grating is custom produced in relation to a reference surface.

5. The moire interferometry system as defined in claim 1 further comprising a condenser lens optically coupled to the light source for providing directional light rays.

6. The moire interferometry system as defined in claim 1 wherein said light source produces white light rays.

7. A moire interferometry system for measuring the shape of a contoured surface, said system comprising:

a projection system including a light source, a first diffraction grating and an imaging lens for projecting grating lines onto the contoured surface, said imaging lens being tilted with respect to the contoured surface; and a viewing system including a second diffraction grating having an array of grating lines and means for viewing the projected grating lines on said surface through said second diffraction grating within an extended depth of view of image, wherein said second diffraction grating is a customized phase grating that is formed with respect to a reference surface and compensates for variations caused by the imaging lens being tilted, the intersection of the projected lines on the surface and the lines on the submaster grating producing moire fringes.

8. The moire interferometry system as defined in claim 7 wherein said first periodic grating comprises an array of square wave grating lines.

9. The moire interferometry system as defined in claim 8 wherein said imaging lens filters out higher diffracted orders of light passing through the first periodic grating so as to produce an array of sine wave lines for projection onto the surface.

10. The moire interferometry system as defined in claim 7 wherein said means for viewing includes a camera focused within the extended depth of view of image.

11. The moire interferometry system as defined in claim 7 wherein said projection system further comprises a condenser lens optically coupled to the light source for providing directional light rays.

12. A method for measuring shape of a contoured surface using moire interferometry, said method comprising the steps of:

projecting a directional light beam through a first diffraction grating having an array of square wave grating lines so as to produce square wave lines;

filtering higher order diffraction orders from said square wave lines with an imaging lens having a selected modulation transfer function so as to pass a sine wave like pattern;

focusing said sine wave like pattern onto the contoured surface; and viewing the sine wave like pattern on the contoured surface through a second diffraction grating within an extended depth of view of image so that the intersection of the projected lines on the surface and lines of the second diffraction grating produce moire fringes.

13. The method as defined in claim 12 further comprising the step of focusing a camera within the extended depth of view of image that is produced by an interference pattern as seen through the second diffracted grating.

14. The method as defined in claim 12 further comprising the step of tilting the imaging lens with respect to the contoured surface so as to permit viewing at an angle in excess of a field angle of the imaging lens.

15. The method as defined in claim 12 further comprising the step of custom recording the second diffraction grating while viewing the grating projection on a reference surface.

16. The method as defined in claim 12 further comprising the step of collecting light rays emitted by a light source to produce the directional light rays.

17. A method for measuring shape of a contoured surface using moire interferometry, said method comprising the steps of:

projecting a directional light beam through a first diffraction grating so as to produce grating lines of light;

focusing said grating lines of light through an imaging lens and onto the contoured surface, said imaging lens being tilted with respect to the contoured surface;

viewing the projection of grating lines on the contoured surface through a second diffraction grating so that the intersection of the projected lines on the surface and lines of the second diffraction grating produce moire fringes, wherein said second diffraction grating is a phase grating that is custom produced in relation to a reference surface and compensates for variations caused by the imaging lens being tilted.

18. The method as defined in claim 17 wherein said step of projecting directional light through the first diffraction grating produces an array of square wave grating lines.

19. The method as defined in claim 18 further comprising the step of filtering higher diffracted orders of said square wave grating lines so as to produce an array of sine wave like lines.

* * * * *